United States Patent [19]
Imran

[11] Patent Number: 5,327,889
[45] Date of Patent: Jul. 12, 1994

[54] MAPPING AND ABLATION CATHETER WITH INDIVIDUALLY DEPLOYABLE ARMS AND METHOD

[75] Inventor: Mir A. Imran, Palo Alto, Calif.

[73] Assignee: Cardiac Pathways Corporation, Sunnyvale, Calif.

[21] Appl. No.: 983,968

[22] Filed: Dec. 1, 1992

[51] Int. Cl.⁵ .............................................. A61B 5/04
[52] U.S. Cl. ..................................... 128/642; 607/122
[58] Field of Search ................ 128/642; 607/122, 119, 607/123, 125, 126, 128, 130

[56] References Cited

U.S. PATENT DOCUMENTS

| | | | |
|---|---|---|---|
| 4,522,212 | 6/1985 | Gelinas et al. | 607/122 X |
| 4,940,064 | 7/1990 | Desai | 607/122 |
| 5,010,894 | 4/1991 | Edhag | 607/128 |
| 5,127,421 | 7/1992 | Bush et al. | 607/130 |
| 5,237,996 | 8/1993 | Waldman et al. | 128/642 |

OTHER PUBLICATIONS

"Metals That Remember", James Hanson, Science '81 pp. 44-46, Jun. 1981.

*Primary Examiner*—Lee S. Cohen
*Assistant Examiner*—Jeffrey R. Jastrzab
*Attorney, Agent, or Firm*—Flehr, Hohbach, Test Albritton & Herbert

[57] ABSTRACT

A catheter comprising a flexible elongate tubular member having proximal and distal extremities. A deflection tip is carried by the distal extremity of the flexible elongate member and has a curved deflecting surface. The flexible elongate member has a plurality of lumens therein extending through the distal extremity of the flexible elongate member and opening onto the curved deflecting surface of the deflecting tip. A plurality of arms are slidably mounted in the lumens. Each of the arms has a plurality of electrodes spaced-apart longitudinally thereon. A control mechanism is secured to the proximal extremity of the flexible elongate member and is coupled to the plurality of arms for moving the distal extremities of the arms into engagement with the deflection tip to cause the arms to deflect proximally and outwardly from the deflection tip.

18 Claims, 3 Drawing Sheets

MAPPING AND ABLATION CATHETER WITH INDIVIDUALLY DEPLOYABLE ARMS AND METHOD

BACKGROUND OF THE INVENTION

In U.S. Pat. No. 5,156,151, there is disclosed a basket-like construction which is provided with a plurality of circumferentially spaced-apart arms which have outer surfaces on which a plurality of electrodes are spaced-apart longitudinally. The proximal extremity and the distal extremity of the basket-like construction are each interconnected. In the deployment of such basket-like constructions into the heart, difficulties have been encountered with the arms of the basket interfering with the mitral valve structure in the left ventricle. In addition, it has been found that the basket-like construction has a tendency to interfere with the posterior leaflet and chordae of the mitral valve and thus fails to make good contact with the posterior wall of the left ventricle. Also it has been found and there has been a tendency for the arms to become entangled in the fibrous muscle tissue in the left ventricle preventing proper deployment of the arms of the basket construction. There is therefore a need for a new and improved type of catheter construction which will overcome these difficulties.

SUMMARY OF THE INVENTION

In general, it is an object of the present invention to provide a catheter for mapping and ablation which has individually deployable arms and a method for utilizing said individually deployable arms for mapping and ablation.

Another object of the invention is to provide a catheter of the above character in which the individually deployable arms have distal extremities which are curved.

Another object of the invention is to provide a catheter of the above character in which the distal extremities are curved into pigtails to prevent the arms from becoming entangled in the valve structure within the heart.

Another object of the invention is to provide a catheter of the above character having arms with an element disposed therein having a shape-memory.

Another object of the invention is to provide a catheter of the above character in which each of the arms is provided with an element having a shape-memory.

Another object of the invention is to provide a catheter of the above character in which the individually deployable arms can be deployed to encompass the entire surface of the wall forming the chamber of the heart.

Another object of the invention is to provide a catheter of the above character in which the individually deployable arms can be actuated to fit hearts of different sizes.

Another object of the invention is to provide a catheter of the above character having deployable arms which have a stiffness profile that can be adjusted.

Another object of the invention is to provide a catheter of the above character in which the stiffness of the arms can be adjusted by controlling the amount of current supplied to the shape-memory elements.

Another object of the invention is to provide a catheter of the above character in which a deflection tip is provided for deflecting the arms in direction proximally and outwardly from the distal extremity of the catheter.

Another object of the invention is to provide a catheter of the above character in which the tip deflector is expandable to provide a larger surface area for deflecting the deployable arms.

Another object of the invention is to provide a catheter of the above character having a control mechanism by which the individually deployable arms can be deployed manually.

Additional objects and features of the invention will appear from the following description which the preferred embodiments set forth in detail in conjunction with the accompanying drawings.

DETAILED DESCRIPTION

In general, the catheter incorporating the present invention is comprised of a flexible elongate member having proximal and distal extremities. A deflection tip is carried by the distal extremity and has a curved deflecting surface. The flexible elongate member has a plurality of lumens extending through the distal extremity of the flexible elongate member and an opening into the curved deflecting surface of the deflection tip. A plurality of arms are slidably mounted in the lumens. Each of the arms has an outer surface on which a plurality of electrodes are mounted in spaced-apart longitudinal position. The arms are movable into engagement with the deflecting surface which causes the arms to be deflected proximally and outwardly from the distal extremity of the catheter. Control means is secured to the proximal extremity of the flexible elongate member and is coupled to the arms for causing individual deployment of the arms by advancing and retracting the arms with respect to the deflectable tip.

Figures 5, 6:
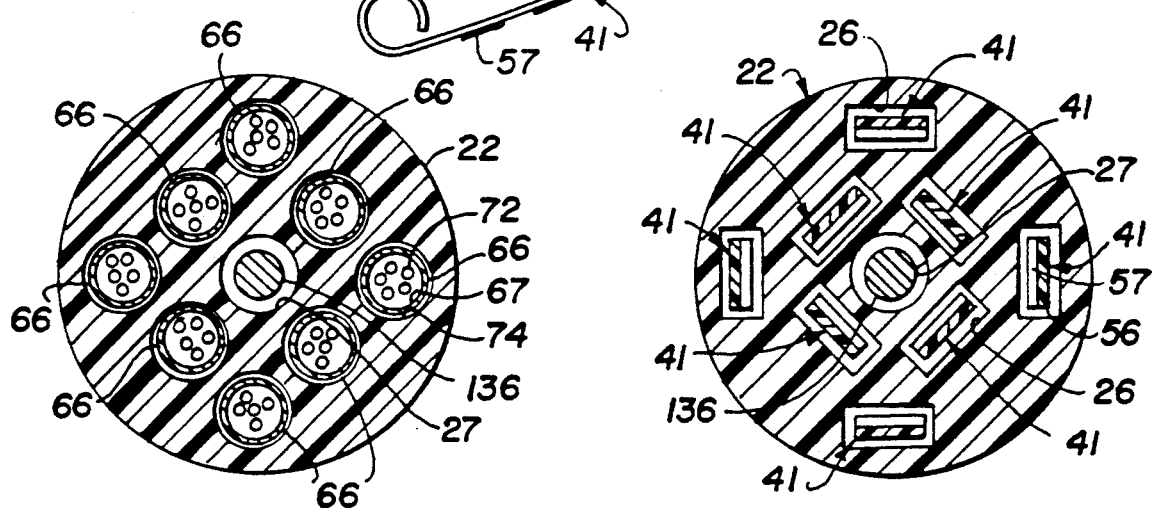
FIG. 5 is a cross-sectional view taken along line 5—5 of FIG. 4.
FIG. 6 is a cross-sectional view taken along line 6—6 of FIG. 4.

More in particular, the catheter 21 incorporating the present invention consists of a flexible elongate member 22 which is provided with proximal and distal extremities 23 and 24. The flexible elongate member 22 is formed of a suitable material such as plastic and can have a size ranging from 3 French to 12 French. The distal extremity 24 of the catheter is provided with a plurality of lumens 26. As for example, eight of such lumens 26 can be provided which can be rectangular in cross section as shown, the lumens 26 are arranged in two groups or sets with one set of four being disposed near the outer perimeter of the flexible elongate member 22 and the other set of four being disposed inwardly and offset circumferentially to the first set particularly as shown in FIG. 6.

Figure 1:
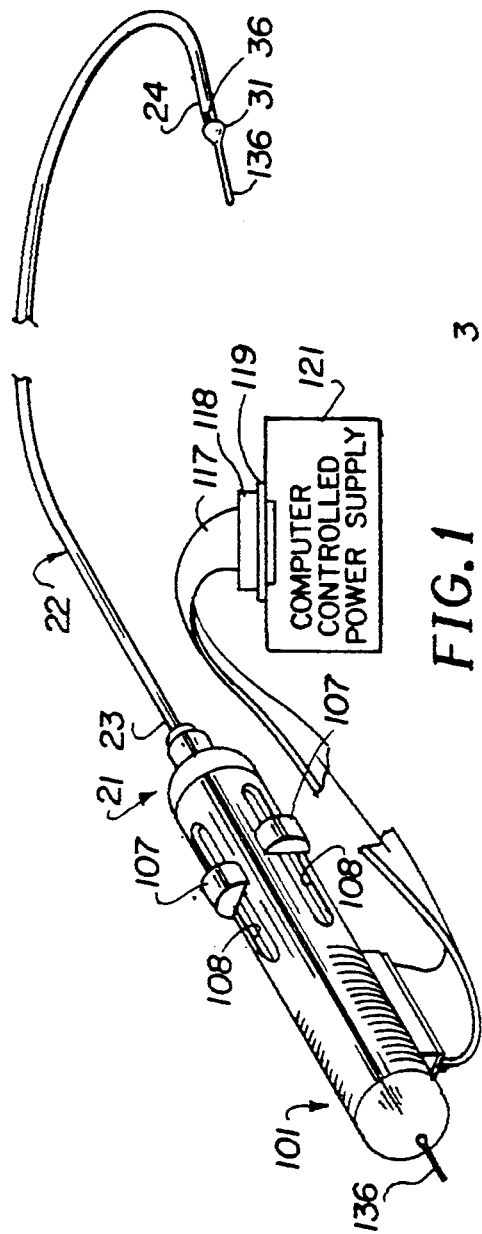
FIG. 1 is a symmetric view showing a catheter having individually deployable arms incorporating the present invention.
Figure 2:
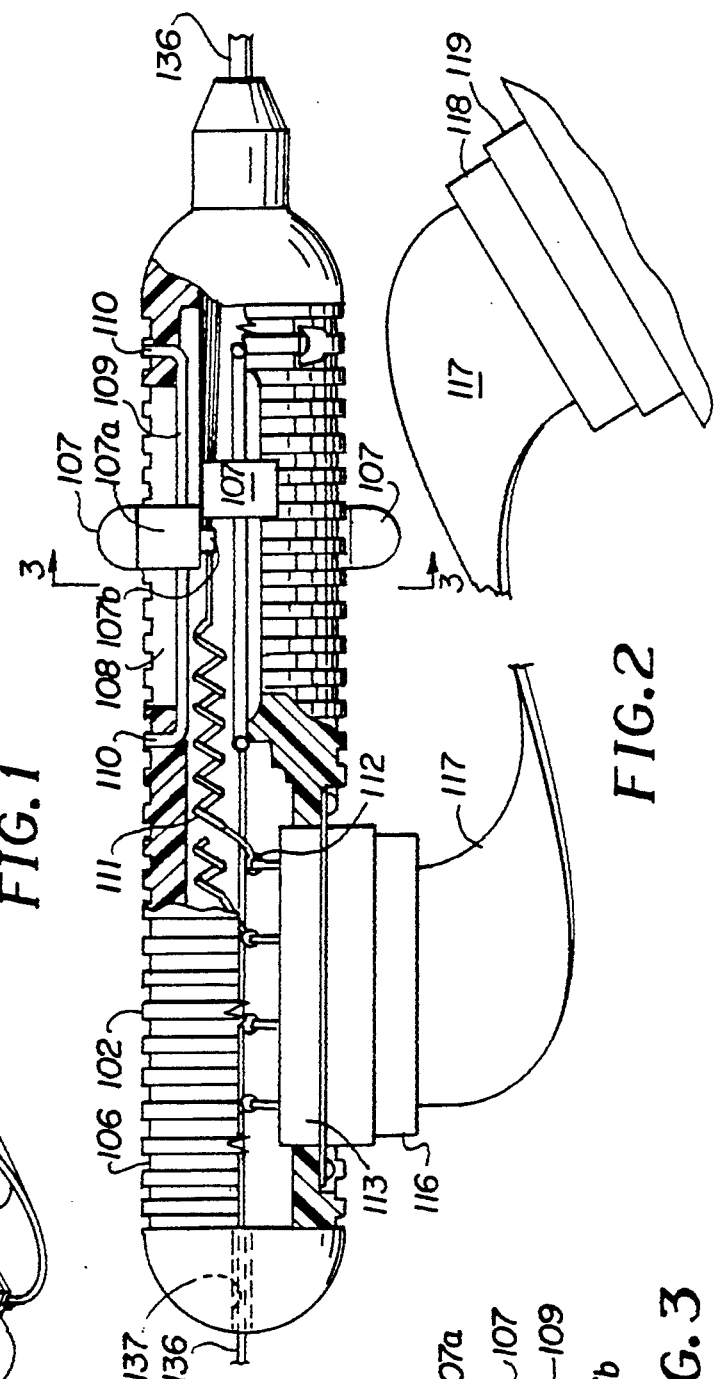
FIG. 2 is a side elevational view partially in cross-section showing the hand-held control device forming a part of the catheter which is utilized for operating the individually deployable arms.
Figure 3:
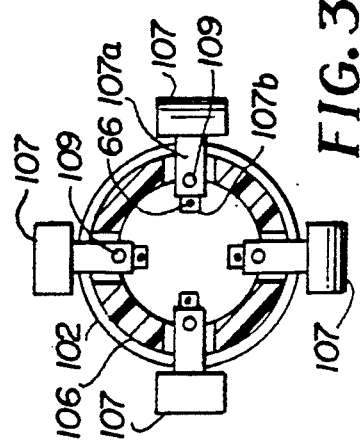
FIG. 3 is a cross-sectional view taken along line 3—3 of FIG. 2.
Figure 4:
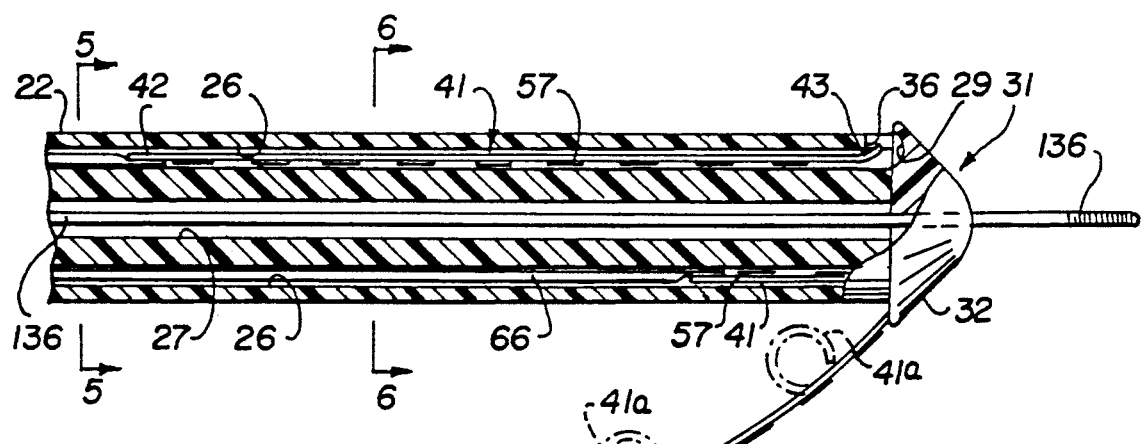
FIG. 4 is a cross-sectional view of the distal extremity of a catheter shown in FIG. 1 showing one of the individually deployable arms being deployed.

An additional central lumen 27 is provided which serves as a guide wire lumen. The lumens 26 open onto curved surfaces 29 which are provided on a deflection tip 31. The deflection tip 31 is formed of a suitable material such as plastic and is secured to the distal extremity 24 of the flexible elongate member 22 by suitable means such as an adhesive. The deflection tip 31 is provided with a rounded outer surface 32 as shown particularly in FIG. 4. The distal extremity 24 is provided with a plurality circumferentially spaced holes 36 immediately adjacent the curved surfaces 29 which extend radially from the flexible elongate member 22.

Figure 7:
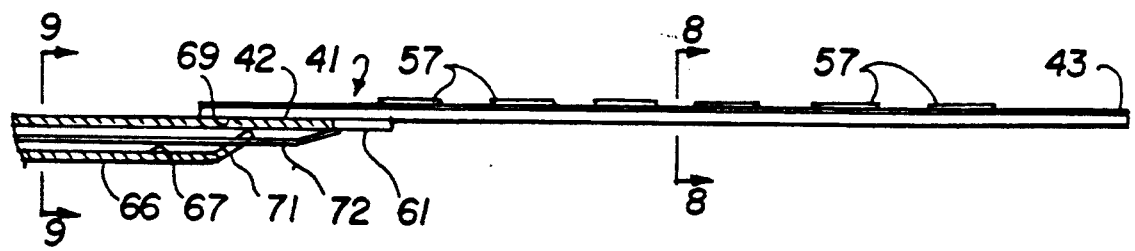
FIG. 7 is an enlarged detail view of one of the deployable arms of the catheter.
Figure 8:
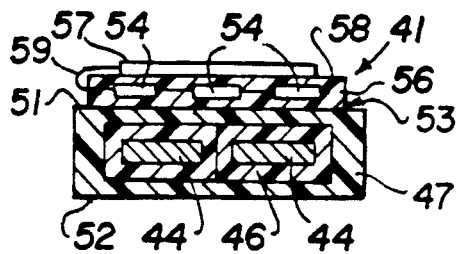
FIG. 8 is a cross-sectional view taken along the line 8—8 of FIG. 7.
Figure 9:
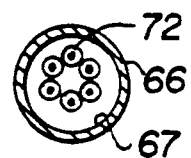
FIG. 9 is a cross-sectional view taken along the line 9—9 of FIG. 7.

A plurality of individually deployable arms 41 are provided in the lumens 26 and are slidably mounted therein. The arms have proximal and distal extremities 42 and 43. One of the arms 41 is shown in FIGS. 7 and 8 and as shown therein consists of a pair of spaced-apart flexible elements or ribbons 44 formed of a shape-memory alloy, as for example Nitinol which extend longitudinally of the arm. Such elements have been programmed with a memory which when an electrical current is supplied to the same to increase their temperature they stiffen and become straight. The transition temperature is set slightly higher than body temperature of 37° C., as for example 42°–45° C. By way of example, the ribbons can have a thickness of 0.005 inches and a width of 0.020 inches. Alternatively, the shape memory elements can be made of a superelastic material which do not require heating to achieve the desired characteristic.

The individual ribbons 44 are covered by a layer 46 of insulating material. The two ribbons 44 are formed into a unitary assembly by another layer 47 of a suitable insulating material as for example a polyimide or polyurethane insulation. The insulation layer 47 provides an outer surface 51 and an inner surface 52. A flex circuit 53 is carried by the outer surface 51 which consists of a plurality of transversely spaced-apart conductors 54 extending longitudinally of the arm and which are insulated from each other by a carrier 56 formed of a suitable plastic material. A plurality of electrodes 57 are provided on an outer surface 58 of the carrier 56 and are spaced-apart longitudinally of the arm as shown in FIG. 7. The electrodes 57 are formed of a suitable conductive material such as silver-clad copper. The electrodes 57 adhere to the surface 58 and are connected by leads 59 to the conductors 54. Thus, each one of the electrodes 57 is connected to one of the conductors 54. The conductors 54 on each arm 41 are connected to a semiconductor chip 61 mounted on the same arm.

The proximal extremity 42 of each of the arms 41 is secured to a tubular member 66 formed of a suitable material such as stainless steel or Nitinol. It is provided with a passage or bore 67 extending therethrough. The tubular member 66 is provided with proximal and distal extremities 68 and 69. The distal extremity 69 has a cutout 71 provided therein and is secured to the proximal extremity 42 of the arm 41 by suitable means such as an adhesive (not shown). A plurality of insulated conductors 72 extend through the passage 67 of the tubular member 66 and are connected to semiconductor chip 61. The tubular members 66 extend through lumens 74 circumferentially spaced around the central lumen 27 of the flexible elongate tubular member 22 to the proximal extremity 23.

A hand-held control unit 101 is mounted on the proximal extremity 23 of the flexible elongate member 22 and forms a part of the catheter 21. The control unit 101 consists of a two-part housing 102 which is formed of a suitable material such as plastic. The housing 102 is sized so that it can readily fit in the human hand and for example can have a diameter approximately of 1 inch and a length of 5 inches. The housing 102 is provided with a plurality of circumferentially extending annular recesses 106 which are spaced-apart longitudinally of the housing 102 to aid the hand gripping the housing 102.

Means is carried by the housing 102 to cause the sliding movement of the individually deployable arms 41 and consists of a plurality of circumferentially spaced-apart knobs or control members 107. The control members 107 protrude from the housing and are generally semi-circular as shown and travel in slots 108 spaced-apart circumferentially of housing 102 and extending longitudinally of the housing. As can be seen four control members 107 with four slots 108 have been provided for the eight deployable arms 41 provided in the flexible elongate member 22. In the present embodiment for each control member 107 two of the arms 41 are controlled thereby. The slots 108 have a length which corresponds to the length of the arms 41. The control members 107 are provided with extensions 107a which extend through the slots 108 and extensions 107b that are slidably mounted on U-shaped rods 109 which underlie the slots 108. The ends of the U-shaped rod 109 are secured to the housing by suitable means such as holes 110 receiving the ends and an adhesive (not shown).

Each of the control members 107 is provided with a protrusion 107b which is secured to two adjacent tubular members 66 and in which the conductors extending therefrom are connected via spring-like conductive strain relief coils 111 connected to terminals 112 of a female receptacle mounted in the housing 102. The other control members 107 are connected to the other tubular members 66 and to the female receptacle 113 in a similar manner. A male connector 116 is mounted in the female connector and is connected to a flexible tape cable 117. The tape cable 117 is connected to another male connector 118 which mates with a female connector 119 provided in a computer controlled power supply for supplying energy to the arms 41.

The catheter 21 is adapted to accommodate a steerable guide wire 136 of a conventional type as for example a 0.032" guide wire which extends through a passage 137 provided in the housing 102 and through the central lumen 27 in the flexible elongate member 22 and through the deflection tip 31.

Figure 11:
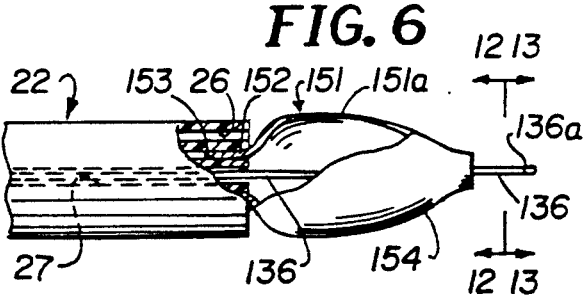
FIG. 11 is another embodiment of the catheter incorporating the present invention partially in cross-section in which an expandable deflection tip is provided shown in an unexpanded form.

Operation and use of the catheter 21 may now be described as follows. Let it be assumed that it is desired to perform a mapping procedure in the left ventricle of the human heart. The guide wire 136 is advanced into the femoral artery of the patient in a conventional manner. The guide wire 136 is advanced into the heart 137 as shown in FIG. 11 by advancing the distal extremity of the guide wire through the aorta passing it through the aortic valve 138 then to the apex 139 of the left ventricle 141. As soon as the guide wire 136 has been properly positioned, the catheter 21 is taken and its distal extremity with its tip 32 is advanced over the guide wire 136 into the femoral artery and into the same route taken by the guide wire so that the deflection tip 31 is brought into contact with the apex 139 of the right ventricle 141. The guide wire 136 can then be withdrawn. The arms 41 can then be deployed to bring them into engagement with wall 142 of the heart forming the right ventricle. To accomplish this deployment the cardiologist grasps the control unit 101 and by utilizing one or more fingers of the hand engages of the knobs or control members 107 and pushes them toward the distal extremity of the housing 102 singularly or in unison.

It should be appreciated with the construction herein before described there are two of the arms 41 connected to each of the control members 107. If desired a separate control member 107 can be provided for each arm 107. Thus, let it be assumed that one of the control members 107 is advanced and as it is advanced, the tubular members 66 secured thereto and the arms 41 secured to the tubular members 66 cause the distal extremities of the arms 41 to be moved forwardly or distally until they engage the curved surfaces of the deflector tip 31 to deflect the outer or distal extremities of the arms 41 out through the holes 36 provided in the flexible elongate member 22. As they exit through the holes 36, the distal extremities of the arms assume a pigtail-like conformations 41a which are curved through approximately 360° and at least 160° as the distal extremities of the arms 41 come in contact with the heat of the blood of the patient. These curved portions 41a of the arms 41 serve to prevent the arms 41 from becoming entangled in anatomic structures within the chamber of the heart as for example in the right ventricle. As the arms 41 are advanced through the holes 31 power can be supplied from the computer controlled power supply 121 to the portions of the elements 44 provided in the arms 41 having a transition temperature above body temperature so that they stiffen and become straight.

This straightening will cause the arms 41 to move outwardly so that the spaced-apart electrodes 51 carried thereby are moved into engagement with the wall of the heart. The desired stiffness of the arms can be achieved in a number of ways. For example, it can be increased by changing the amount of current which is going through the ribbons 64 in the arm. Alternatively, it also can be changed by tapering the thickness or the width of the ribbons 44 so that there will be less resistance and therefore less heating where the mass of the element is greater.

Figure 10:
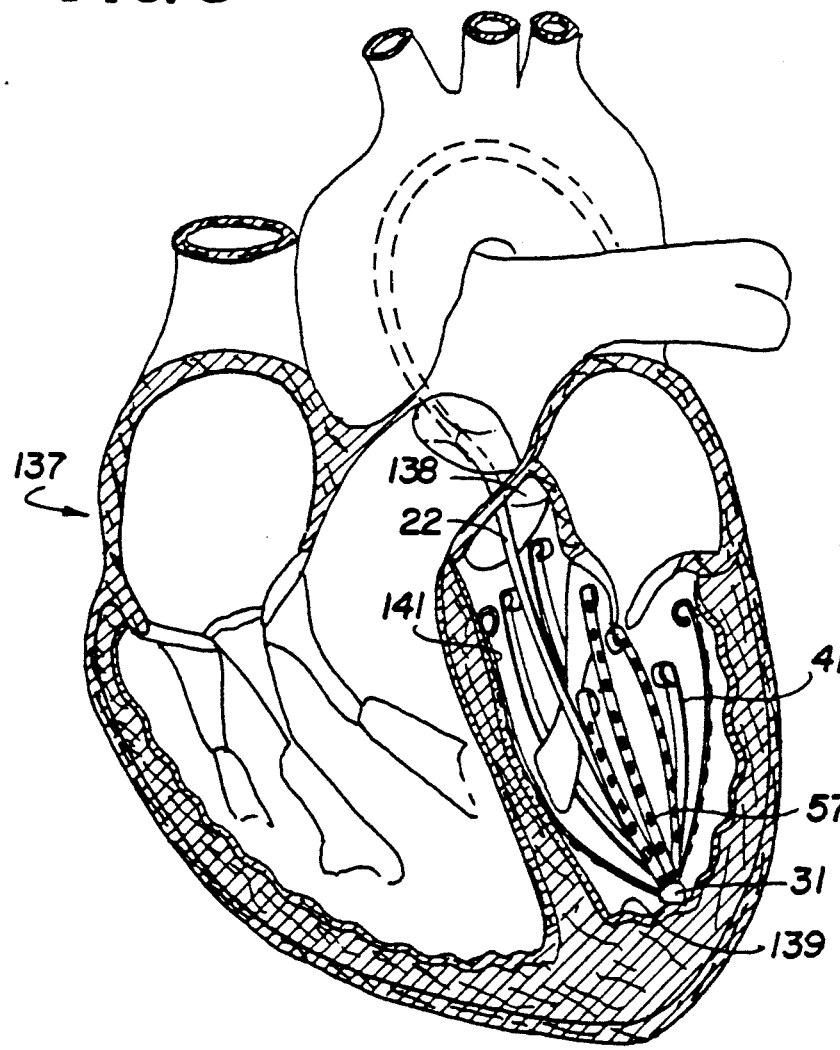
FIG. 10 is a isometric view showing the distal extremity of the catheter disclosed in the right ventricle of the heart with all of the arms being deployed and being in engagement with an encompassing all the wall forming the right ventricle of the heart.

The other individual arms 41 of the catheter 21 can be individually deployed in the same manner as herein before described. As shown in FIG. 10, the arms 41 can be deployed to various lengths so that substantially the entire wall of the chamber is contacted by the electrodes 57 carried by the individually deployed arms 41. The arms 41 can be deployed at two different lengths to make this coverage possible. This can be seen in FIG. 10. The heart signals sensed by the electrodes 57 can then be recorded in the manner described in U.S. Pat. No. 5,156,151 within a single beat of the heart.

It should be appreciated that although the catheter has been described for a mapping operation, it is possible to utilize one of the individually deployed arms to serve as an arm for performing an ablation. For example, let it be assumed that the site to be ablated is discovered to be between two of the arms. When that is the case, the arm opposite those two arms can become a steerable catheter and be moved into the ablation site by causing the arm to move one of its electrodes into contact with the ablation site. Thereafter energy is supplied to that electrode of cause ablation to the wall of the heart to attempt to destroy the aberrant pathway which is causing the arrhythmia.

It should be appreciated that if necessary, after an ablation has been performed and additional mapping is performed with the arms 41 in the same position in the ventricle to ascertain whether or not the ablation eliminated the site for the arrhythmia. If it is found there is still other sites present which are causing arrhythmias, the same procedure can be utilized until all of the arrhythmias are eliminated.

After the ablation has been accomplished, the arms 41 can be de-energized and then can be withdrawn back into the tubular member 22 by operation of the control members 107 by retracting them by the fingers of the hand holding the control unit 101 either one at a time or in unison as desired. Thereafter, the catheter 21 can be withdrawn and the entrance to the femoral artery sutured.

In applications of the present invention when it is desired to utilize a deflecting tip having a greater deflecting surface to deflect the arms in the desired direction, an expandable deflection tip 151 can be provided. The expandable deflection tip 151 can be formed of a suitable material such as thin wall plastic tube of a suitable material such as polyurethane or teflon which has its proximal end 152 mounted in an annular recess 153 provided on the distal extremity 24 of the flexible elongate member 22 and secured therein by suitable means such as an adhesive (not shown). The distal extremity of the plastic tube is swaged inwardly as shown to form an oval shaped opening 156 (see FIG. 12) through which the guide wire 136 extends. The guide wire 136 of the present invention is provided with an enlarged end portion 136 which also is oval shaped but which is of a size slightly less than the size of the oval-shaped opening 156 so that the guide wire can be withdrawn when it is aligned with the opening 156 as hereinafter described. The thin wall tube which is utilized for forming the deflection tip 151 is provided with a weakened region of reduced cross section extending circumferentially around the tube substantially equidistant from the proximal and distal extremities 152 and 154.

Figure 12:
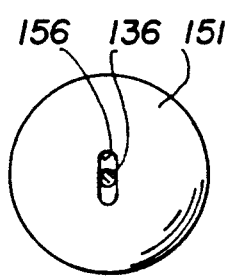
FIG. 12 is a cross-sectional view looking along the line 12—12 of FIG. 11.
Figure 14:
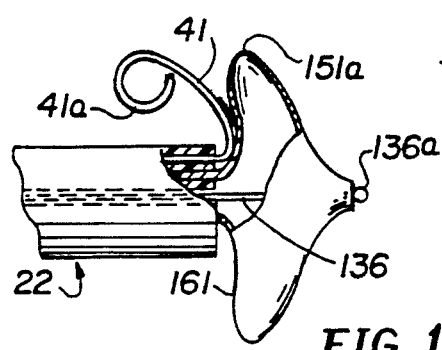
FIG. 14 is a view similar to FIG. 11 but showing the expandable deflection tip in an expanded form.
Figure 13:
FIG. 13 is a cross-sectional view looking along line 13—13 of FIG. 11.

In operation and use of the catheter construction shown in FIGS. 11, 12 and 13, the deflection tip 151 has a diameter which is no greater than the outer diameter of the flexible elongate member 22 and is advanced in the conventional manner by the use of a guide wire 136 first having its distal extremity moved to the desired location and then passing the catheter over the same as hereinbefore described. After the catheter has been moved to the desired location and it is desired to deploy the arms 41, the expandable deflection tip 151 can be expanded by rotating the guide wire 136 so that the oval-shaped tip 136a is rotated into a position which is approximately 90° out of alignment with the oval shaped slot 156. The guide wire 136 is then pulled to bring the oval-shaped tip portion 136a into engagement with the distal extremity 154 and further pulling of the guide wire 136 causes the expandable deflection tip 151 to expand outwardly and radially by bending at the weakened region 158 to provide an umbrella-like shape which has an expanded diameter which is substantially greater than the diameter of the flexible elongate tubular member 22 as shown in FIG. 14. When the tip 151 is expanded in this manner it provides a large diameter radially extending proximally curved surface 161 adapted to be engaged by the deployable arms 41 as they are pushed out of the lumens 26 provided in the flexible elongate member 22 as shown in FIG. 14 and as hereinbefore described in connection with the previous embodiment.

When all of the arms 41 have been deployed and the desired mapping and ablation procedures have been carried out as hereinbefore described, the arms can be retracted. Thereafter, the guide wire 136 can be released to permit the expandable deflection tip 151 to return to its original shape as shown in FIG. 11 by the spring forces generated within the deflection tip 151 so that it returns to its original small diameter to permit ready withdrawal of the catheter after completion of the procedure.

It should be appreciated that because of the construction of the tip 136a of the guide wire it is possible to remove the guide wire by rotating the guide wire so that its oval-shaped tip is in alignment with the oval-shaped opening 156 and then withdrawn therefrom. Since the tip 151 is being urged into engagement with the wall of the heart by the flexible elongate member 22 to which it is attached, it will retain its umbrella-like shape so that the arms 41 can be destroyed in the manner hereinbefore described.

I claim:

1. A catheter for mapping a wall forming a chamber in a heart comprising a flexible elongate tubular member having proximal and distal extremities, a deflection tip carries by the distal extremity of the flexible elongate member and having a curved deflecting surface, said flexible elongate member having a plurality of lumens therein extending through the distal extremity of the flexible elongate member and opening onto the curved deflecting surface of the deflection tip, a plurality of arms slidably mounted in said lumens and having distal extremities, each of said arms having a plurality of electrodes spaced-apart longitudinally thereon and means secured to the proximal extremity of the flexible elongate member and coupled to the plurality of arms for moving the distal extremities of the arms into engagement with the deflection tip for causing the arms to deflect proximally and outwardly from the deflection tip whereby the plurality of electrodes of each of the arms is moved into engagement with the wall to make measurements of the electrical activity in the wall.

2. A catheter as in claim 1, wherein each of said arms is provided with an element extending longitudinally thereof and a having a shape-memory together with conductor means extending from the proximal extremity to the elements in the arms for supplying electrical energy to the arms.

3. A catheter as in claim 2, wherein said element has a distal extremity in the distal extremity of the arm having a shape-memory with a transition temperature which is substantially less than a body temperature of a patient into which the catheter is inserted and having a shape-memory which corresponds to a pigtail so that when an arm is deployed and deflected by the deflection tip, it will assume a curved configuration helping to prevent the distal extremity from becoming entangled in the body.

4. A catheter as in claim 1, wherein said flexible elongate member has a diameter and wherein said deflection tip is expandable and has a diameter substantially greater than the diameter of the flexible elongate tubular member to provide a deflection surface for guiding the arms as they are moved out of the flexible elongate member.

5. A catheter as in claim 4, together with a guide wire extending through the expandable deflection tip, and wherein said expandable deflection tip is formed of a thin-walled tube having proximal and distal extremities having a weakened region intermediate the proximal and distal extremities and being secured to the distal extremity of the flexible elongate member and wherein the guide wire extends through the expandable deflection tip and is formed with a portion which is adapted to be brought into engagement with the distal extremity of the thin-walled tube to cause the tube to collapse along the weakened region to provide an umbrella-like shape having an expanded radially extending proximally curved surface adapted to be engaged by the arms as they are moved out of the flexible elongate tubular member.

6. A catheter as in claim 1, wherein said means secured to the proximal extremity of the flexible elongate member is a control unit consisting of a housing sized so as to be grasped by a human hand, a plurality of control members slidably mounted in said housing and means for connecting said control members through said flexible elongate member to said arms whereby as said control members are operated said arms move into and out of the flexible elongate member.

7. A catheter as in claim 2, wherein said conductor means connected to said elements having a shape-memory include conductors coupled to said control members together with a power supply connected to said conductors.

8. A catheter as in claim 7, wherein said control members are positioned so that they are adapted to be engaged by the fingers of the same hand holding the control unit.

9. A catheter as in claim 8, wherein said control members are spaced circumferentially around the housing.

10. A catheter as in claim 9, wherein one or more of the arms can be individually deployed by actuation of the control members and can be deployed to provide different lengths of arms extending from the flexible elongate tubular member.

11. A catheter for introduction into a chamber of a heart formed by a wall comprising a flexible elongate tubular member having proximal and distal extremities and having a plurality of lumens therein extending longitudinally thereof, a plurality of arms slidably mounted in said lumens, each of said arms having an exterior surface and a distal extremity, a plurality of electrodes mounted on the exterior surface of the arms and being spaced longitudinally of the arms, each of said arms having at least one element therein extending longitudinally thereof having a shape-memory, a deflection tip secured to the distal extremity of the flexible elongate member having a curved deflection surface facing proximally of the flexible elongate tubular member, said deflection surface overlying the lumens so that when the arms are slid out of the lumens they come into engagement with the curved deflection surface and forming means for deflecting the arms proximally and outwardly from the flexible elongate tubular member whereby the plurality of electrodes of each of the arms are moved into engagement with the wall to make measurements of the electrical activity in the wall, a control unit mounted on the proximal extremity of the flexible elongate tubular member and having a housing sized so that it is adapted to be held by a human hand, a plurality of control members slidably mounted on the housing, push/pull elements secured to the control members and extending into the lumens of the flexible elongate member and being secured to the proximal extremities of the arms so that as the control members are actuated, the arms can be moved out of the lumens into engagement with the curved deflection surface so that the electrodes carried by the arms can be moved into engagement with the wall forming the chamber in which the distal extremity of the flexible elongate tubular member is disposed, said push/pull elements carrying conductors in communication with the electrodes carried by the arms and conductors which are connected to the shape-memory elements.

12. A catheter as in claim 11, wherein said push/pull elements are in the form of tubular members having a passage therein and wherein said conductors extend through said passage in said tubular members.

13. A catheter as in claim 11, wherein the heart is disposed in a body having a temperature and wherein each of said arms is provided with an additional shape-memory element located in the distal extremity of each of the arms and having a transition temperature which is substantially below the temperature of the body of the patient and wherein the shape-memory of said additional element is in the form of a pigtail so that when an arm is introduced into the body and is free of obstruction, it will assume a pigtail conformation.

14. An arm comprising a flexible member having proximal and distal extremities, first and second elements disposed in said flexible elongate member at different longitudinal positions in said flexible elongate member, said first and second elements having first and second transition temperatures and electrical conducting means connected to at least one of said first and second elements for supplying electrical energy to at least one of said first and second elements.

15. An arm as in claim 14, wherein said member has an exterior surface together with a plurality of electrodes mounted in spaced-apart positions extending longitudinally of the arm and electrical conducting means connected to said electrodes for carrying electrical signals picked up by the electrodes.

16. An arm as in claim 14, wherein the other of said first and second elements has a transition temperature which is substantially below that of the temperature of a living body.

17. An arm as in claim 16, wherein said other of said first and second elements has a shape-memory which is the form of a pigtail.

18. A method for mapping a chamber of a heart formed by a wall carrying electrical potentials and having an apex by the use of a catheter having a distal extremity with a deflection tip secured to the distal extremity, and having arms slidably mounted therein and movable into engagement with the deflection tip, the method comprising the steps of advancing the distal extremity of the catheter into the chamber of the heart so that the distal extremity comes into engagement with the apex of the chamber, advancing the arms out of the flexible elongate tubular member so that the distal extremity comes into engagement with the deflection tip and urges the arms proximally of the catheter and outwardly therefrom, causing the distal extremities of the arms to form pigtails so that the individual arms will not become entangled within the chamber of the heart, causing the arms to stiffen and move into engagement with the wall of the heart, and advancing the arms to different distances so that substantially all of the wall forming the chamber of the heart is encompassed by electrodes carried by the arms and sensing the electrical potentials which are encountered by electrodes carried by the arms engaging the wall forming the chamber during a single beat of the heart.

* * * * *